(12) United States Patent
Mueller

(10) Patent No.: US 8,540,712 B2
(45) Date of Patent: *Sep. 24, 2013

(54) SURGICAL INSTRUMENT CONFIGURED FOR USE WITH INTERCHANGEABLE HAND GRIPS

(71) Applicant: Covidien LP, Mansfield, MA (US)

(72) Inventor: Peter Michael Mueller, Frederick, CO (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/663,293

(22) Filed: Oct. 29, 2012

(65) Prior Publication Data

US 2013/0053843 A1 Feb. 28, 2013

Related U.S. Application Data

(63) Continuation of application No. 12/859,896, filed on Aug. 20, 2010, now Pat. No. 8,298,233.

(51) Int. Cl.
*A61B 18/00* (2006.01)
(52) U.S. Cl.
USPC .............................. 606/51; 606/52
(58) Field of Classification Search
USPC .................... 606/27, 34, 41, 51, 52
See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| H1745 H | 8/1998 | Paraschac |

(Continued)

FOREIGN PATENT DOCUMENTS

| | | |
|---|---|---|
| CN | 201299462 | 9/2009 |
| DE | 2415263 | 10/1975 |

(Continued)

OTHER PUBLICATIONS

U.S. Appl. No. 08/926,869, filed Sep. 10, 1997, James G. Chandler.

(Continued)

*Primary Examiner* — Michael Peffley
*Assistant Examiner* — Daniel Fowler

(57) ABSTRACT

A surgical instrument is provided and includes a housing having a shaft that extends therefrom that defines a longitudinal axis therethrough, and supports an end effector having opposing jaw members at a distal end thereof. The surgical instrument includes a handle assembly that includes a movable handle and a fixed handle. The fixed handle is adapted to couple to one or more selectively removable grips and the movable handle is configured to impart movement of one or more movable jaw members operably associated with the end effector.

7 Claims, 3 Drawing Sheets

(56) References Cited

U.S. PATENT DOCUMENTS

| | | |
|---|---|---|
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| 6,387,092 B1 * | 5/2002 | Burnside et al. ............... 606/32 |
| H2037 H | 7/2002 | Yates et al. |
| D465,281 S | 11/2002 | Lang |
| D466,209 S | 11/2002 | Bon |
| 6,666,860 B1 * | 12/2003 | Takahashi ...................... 606/34 |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| 7,150,749 B2 * | 12/2006 | Dycus et al. ..................... 606/51 |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| D661,394 S | 6/2012 | Romero et al. |
| 2006/0030845 A1 * | 2/2006 | Leung et al. ..................... 606/41 |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10031773 | 11/2001 |
| DE | 19946527 | 12/2001 |
| DE | 20121161 | 4/2002 |
| DE | 10045375 | 10/2002 |
| DE | 10 2004 026179 | 12/2005 |
| DE | 20 2007 009318 | 8/2007 |
| DE | 20 2007 009165 | 10/2007 |
| DE | 20 2007 009317 | 10/2007 |
| DE | 20 2007 016233 | 3/2008 |
| DE | 19738457 | 1/2009 |
| DE | 10 2008 018406 | 7/2009 |
| EP | 1159926 | 12/2001 |
| JP | 61-501068 | 9/1984 |
| JP | 6-502328 | 3/1992 |
| JP | 5-5106 | 1/1993 |
| JP | 5-40112 | 2/1993 |
| JP | 6-030945 | 2/1994 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-317936 | 3/1996 |
| JP | 8-289895 | 5/1996 |
| JP | 8-252263 | 10/1996 |
| JP | 8-317934 | 12/1996 |
| JP | 9-000538 | 1/1997 |
| JP | 9-10223 | 1/1997 |
| JP | 9-122138 | 5/1997 |
| JP | 10-000195 | 1/1998 |
| JP | 10-24051 | 1/1998 |
| JP | 11-070124 | 5/1998 |
| JP | 10-155798 | 6/1998 |
| JP | 2000-102545 | 9/1998 |
| JP | 11-47150 | 2/1999 |
| JP | 11-169381 | 6/1999 |
| JP | 11-192238 | 7/1999 |
| JP | 11-244298 | 9/1999 |
| JP | 2000-342599 | 12/2000 |
| JP | 2000-350732 | 12/2000 |
| JP | 2001-8944 | 1/2001 |
| JP | 2001-29356 | 2/2001 |
| JP | 2001-128990 | 5/2001 |
| JP | 2001-190564 | 7/2001 |
| JP | 2001-3400 | 11/2001 |
| JP | 2002-528166 | 3/2002 |
| JP | 2002-136525 | 5/2002 |
| JP | 2003-116871 | 4/2003 |
| JP | 2003-175052 | 6/2003 |
| JP | 2003-245285 | 9/2003 |
| JP | 2004-517668 | 6/2004 |
| JP | 2004-528869 | 9/2004 |
| JP | 2005-152663 | 6/2005 |
| JP | 2005-253789 | 9/2005 |
| JP | 2006-015010 | 1/2006 |
| JP | 2006-501939 | 1/2006 |
| JP | 2006-095316 | 4/2006 |
| JP | 2011-125195 | 6/2011 |
| SU | 401367 | 11/1974 |
| WO | WO 00/36986 | 6/2000 |
| WO | WO 00/59392 | 10/2000 |
| WO | WO 01/15614 | 3/2001 |
| WO | WO 01/54604 | 8/2001 |
| WO | WO 02/45589 | 6/2002 |
| WO | WO 2005/110264 | 11/2005 |
| WO | WO 2006/021269 | 3/2006 |
| WO | WO 2008/040483 | 4/2008 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremcich.
U.S. Appl. No. 13/277,373, filed Oct. 20, 2011, Glenn A. Horner.
U.S. Appl. No. 13/277,926, filed Oct. 20, 2011, David M. Garrison.
U.S. Appl. No. 13/277,962, filed Oct. 20, 2011, David M. Garrison.
U.S. Appl. No. 13/293,754, filed Nov. 10, 2011, Jeffrey M. Roy.
U.S. Appl. No. 13/306,523, filed Nov. 29, 2011, David M. Garrison.
U.S. Appl. No. 13/306,553, filed Nov. 29, 2011, Duane E. Kerr.
U.S. Appl. No. 13/308,104, filed Nov. 30, 2011, John R. Twomey.
U.S. Appl. No. 13/312,172, filed Dec. 6, 2011, Robert J. Behnke, II.
U.S. Appl. No. 13/324,863, filed Dec. 13, 2011, William H. Nau, Jr.
U.S. Appl. No. 13/344,729, filed Jan. 6, 2012, James D. Allen, IV.
U.S. Appl. No. 13/355,829, filed Jan. 23, 2012, John R. Twomey.

U.S. Appl. No. 13/357,979, filed Jan. 25, 2012, David M. Garrison.
U.S. Appl. No. 13/358,136, filed Jan. 25, 2012, James D. Allen, IV.
U.S. Appl. No. 13/360,925, filed Jan. 30, 2012, James H. Orszulak.
U.S. Appl. No. 13/400,290, filed Feb. 20, 2012, Eric R. Larson.
U.S. Appl. No. 13/404,435, filed Feb. 24, 2012, Kim V. Brandt.
U.S. Appl. No. 13/404,476, filed Feb. 24, 2012, Kim V. Brandt.
U.S. Appl. No. 13/412,879, filed Mar. 6, 2012, David M. Garrison.
U.S. Appl. No. 13/412,897, filed Mar. 6, 2012, Joanna Ackley.
U.S. Appl. No. 13/421,373, filed Mar. 15, 2012, John R. Twomey.
U.S. Appl. No. 13/430,325, filed Mar. 26, 2012, William H. Nau, Jr.
U.S. Appl. No. 13/433,924, filed Mar. 29, 2012, Keir Hart.
U.S. Appl. No. 13/448,577, filed Apr. 17, 2012, David M. Garrison.
U.S. Appl. No. 13/460,455, filed Apr. 30, 2012, Luke Waaler.
U.S. Appl. No. 13/461,335, filed May 1, 2012, James D. Allen, IV.
U.S. Appl. No. 13/461,378, filed May 1, 2012, James D. Allen, IV.
U.S. Appl. No. 13/461,397, filed May 1, 2012, James R. Unger.
U.S. Appl. No. 13/461,410, filed May 1, 2012, James R. Twomey.
U.S. Appl. No. 13/466,274, filed May 8, 2012, Stephen M. Kendrick.
U.S. Appl. No. 13/467,767, filed May 9, 2012, Duane E. Kerr.
U.S. Appl. No. 13/470,775, filed May 14, 2012, James D. Allen, IV.
U.S. Appl. No. 13/482,589, filed May 29, 2012, Eric R. Larson.
U.S. Appl. No. 13/483,733, filed May 30, 2012, Dennis W. Butcher.
U.S. Appl. No. 13/537,517, filed Jun. 29, 2012, David N. Heard.
U.S. Appl. No. 13/537,577, filed Jun. 29, 2012, Tony Moua.
U.S. Appl. No. 13/663,317, filed Oct. 29, 2012, Unger.
U.S. Appl. No. 13/708,335, filed Dec. 7, 2012, Dumbauld.
U.S. Appl. No. 13/711,201, filed Dec. 11, 2012, Regadas.
U.S. Appl. No. 13/736,650, filed Jan. 8, 2013, McKenna.
U.S. Appl. No. 13/741,550, filed Jan. 15, 2013, Deborski.
U.S. Appl. No. 13/747,090, filed Jan. 22, 2013, Romero.
U.S. Appl. No. 13/747,167, filed Jan. 22, 2013, Romero.
U.S. Appl. No. 13/731,674, filed Dec. 31, 2012, Siebrecht.
U.S. Appl. No. 13/799,173, filed Mar. 13, 2013, Larson.
U.S. Appl. No. 13/803,636, filed Mar. 14, 2013, Kerr.
U.S. Appl. No. 13/803,762, filed Mar. 14, 2013, Kerr.
U.S. Appl. No. 13/803,884, filed Mar. 14, 2013, Kerr.
U.S. Appl. No. 13/804,010, filed Mar. 14, 2013, Kerr.
U.S. Appl. No. 13/833,823, filed Mar. 15, 2013, Garrison.
U.S. Appl. No. 13/834,703, filed Mar. 15, 2013, Garrison.
U.S. Appl. No. 13/835,004, filed Mar. 15, 2013, Twomey.
U.S. Appl. No. 13/838,945, filed Mar. 15, 2013, Stoddard.
U.S. Appl. No. 13/853,259, filed Mar. 29, 2013, Garrison.
U.S. Appl. No. 13/853,273, filed Mar. 29, 2013, Kerr.
U.S. Appl. No. 13/853,339, filed Mar. 29, 2013, Reschke.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.

Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.

Crawford et al. "Use of the LigaSure Vessel Sealing System in Urologic Cancer Surgery" Grand Rounds in Urology 1999 vol. 1 Issue 4 pp. 10-17.

Craig Johnson, "Use of the LigaSure Vessel Sealing System in Bloodless Hemorrhoidectomy" Innovations That Work, Mar. 2000.

Levy et al. "Use of a New Energy-based Vessel Ligation Device During Vaginal Hysterectomy" Int'l Federation of Gynecology and Obstetrics (FIGO) World Congress 1999.

Barbara Levy, "Use of a New Vessel Ligation Device During Vaginal Hysterectomy" FIGO 2000, Washington, D.C.

E. David Crawford "Use of a Novel Vessel Sealing Technology in Management of the Dorsal Veinous Complex" Sales/Product Literature 2000.

Jarrett et al., "Use of the LigaSure Vessel Sealing System for Peri-Hilar Vessels in Laparoscopic Nephrectomy" Sales/Product Literature 2000.

Crouch et al. "A Velocity-Dependent Model for Needle Insertion in Soft Tissue" MICCAI 2005; LNCS 3750 pp. 624-632, Dated: 2005.

McLellan et al. "Vessel Sealing for Hemostasis During Pelvic Surgery" Int'l Federation of Gynecology and Obstetrics FIGO World Congress 2000, Washington, D.C.

McLellan et al. "Vessel Sealing for Hemostasis During Gynecologic Surgery" Sales/Product Literature 1999.

* cited by examiner

SURGICAL INSTRUMENT CONFIGURED FOR USE WITH INTERCHANGEABLE HAND GRIPS

CROSS-REFERENCE TO RELATED APPLICATIONS

The present application is a continuation of U.S. patent application Ser. No. 12/859,896, now U.S. Pat. No. 8,298,233, filed on Aug. 20, 2010, the entire contents of each of which is hereby incorporated by reference herein.

BACKGROUND

1. Technical Field

The present disclosure relates to surgical instruments and, more particularly, to surgical instruments configured for use with interchangeable hand grips.

2. Description of Related Art

Surgical instruments, e.g., electrosurgical forceps (closed type), are well known in the medical arts and typically include a housing, a handle assembly, a shaft and an end effector assembly attached to a distal end of the shaft. In certain instances, the handle assembly may include one or more fixedly attached hand grips that provide a gripping surface for an operator, e.g., a clinician, such that the operator may securely and comfortably grasp the surgical instrument. To this end, the handle assembly including the hand grips are appropriately sized, shaped and equipped to improve the operator's hold on the surgical instrument.

In certain instances, the surgical instrument may include one or more functional features, e.g., a rotating assembly, which may be configured to facilitate operation thereof. The one or more features are, typically, actuatable from the handle and/or hand grip assemblies. For example, to facilitate operation of a rotating assembly that may be used to rotate a shaft of the surgical instrument, the rotating assembly is positioned on a housing of the surgical instrument and within a "finger's reach" of the handle and/or hand grip assemblies.

To accommodate various hand sizes, in addition to left or right hand use, manufactures typically produce the same surgical instrument with multiple molded or overmolded handle and/or hand grip assemblies. As can be appreciated, this may not be cost effective. Moreover, repositioning of the one or more functional features on the surgical instrument may be required to accommodate the multiple configurations of handle and/or hand grip assemblies.

SUMMARY

The present disclosure provides a surgical instrument. The surgical instrument includes a housing having a shaft that extends therefrom that defines a longitudinal axis therethrough, and supports an end effector having opposing jaw members at a distal end thereof. The surgical instrument includes a handle assembly that includes a movable handle and a fixed handle. The fixed handle is adapted to couple to one or more selectively removable grips and the movable handle is configured to impart movement of one or more movable jaw members operably associated with the end effector.

The present disclosure also provides an electrosurgical system for performing an electrosurgical procedure. The electrosurgical system includes an electrosurgical generator that includes a control system. An electrosurgical instrument is adapted to couple to the electrosurgical generator and includes a housing having a shaft that extends therefrom that defines a longitudinal axis therethrough, and supports an end effector having opposing jaw members at a distal end thereof. The surgical instrument includes a handle assembly that includes a movable handle and a fixed handle. The fixed handle is adapted to couple to one or more selectively removable grips and the movable handle is configured to impart movement of one or more movable jaw members operably associated with the end effector.

BRIEF DESCRIPTION OF THE DRAWING

Various embodiments of the present disclosure are described hereinbelow with references to the drawings, wherein.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1:
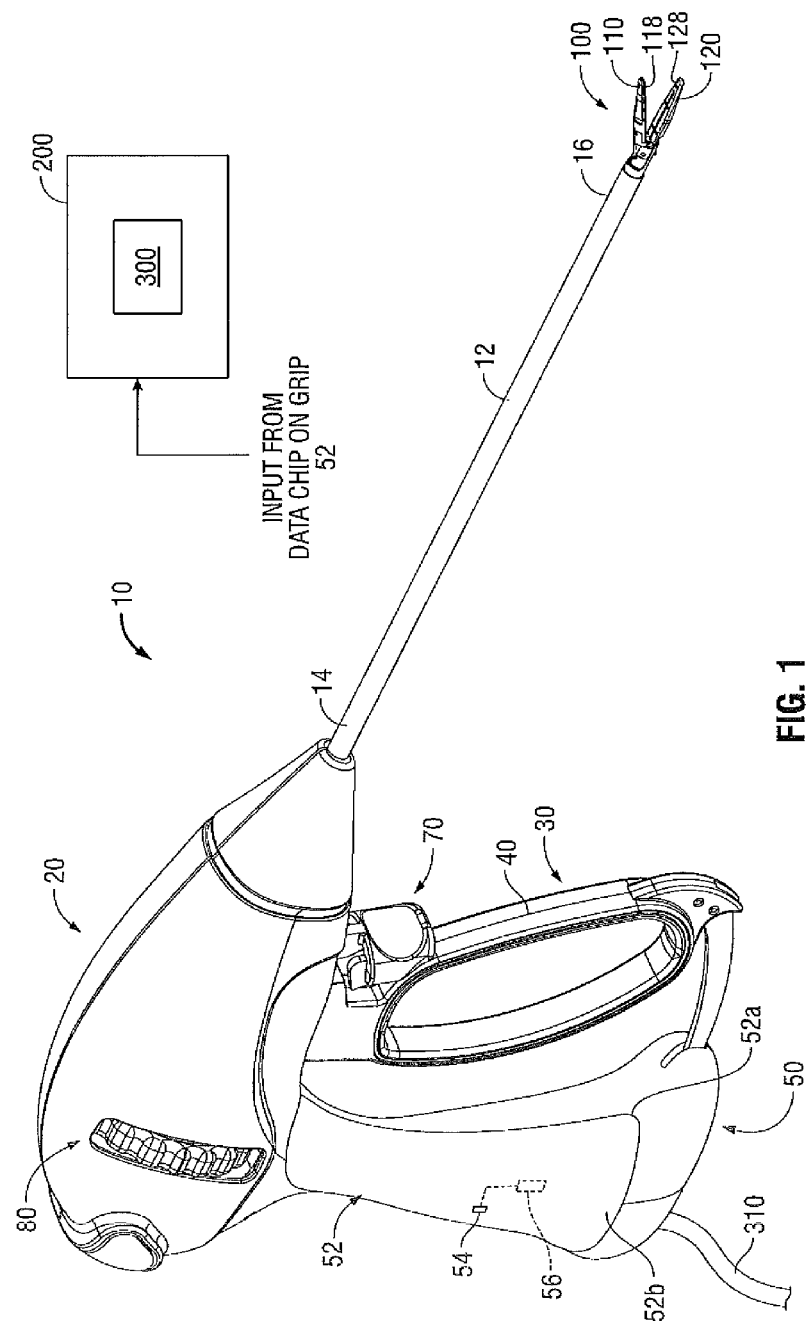
FIG. 1 is a side, perspective view of a surgical instrument that includes a handle assembly including a selectively removable hand grip according to an embodiment of the present disclosure.

With reference to FIG. 1, an illustrative embodiment of a surgical instrument 10, e.g., a forceps 10, that includes one or more selectively removable grips 52 is shown. Forceps 10 is adapted to operatively and selectively couple to an electrosurgical generator 200 for performing an electrosurgical procedure. For purposes herein, an electrosurgical procedure may include sealing, cutting, cauterizing coagulating, desiccating, and fulgurating tissue all of which may employ RF energy. Generator 200 may be configured for monopolar and/or bipolar modes of operation. Generator 200 includes (or is in operative communication with) a system 300 that may include one or more processors in operative communication with one or more control modules that are executable on the processor. The control module (not explicitly shown) may be configured to instruct one or more modules to transmit electrosurgical energy, which may be in the form of a wave or signal/pulse, via one or more cables (e.g., a cable 310) to one or both seal plates 118, 128 associated with the forceps 10.

Briefly, forceps 10 is shown configured for use with various electrosurgical procedures and generally includes a housing 20, an electrosurgical cable 310 that connects the forceps 10 to the generator 200, a rotating assembly 80, a trigger assembly 70, and handle assembly 30 in operative communication with a drive assembly 130 (FIG. 3) for imparting movement of one or both of a pair of jaw members 110, 120 of an end effector assembly 100 operably associated with the forceps 10.

Forceps 10 includes a shaft 12 that has a distal end 16 configured to mechanically engage the end effector assembly 100 and a proximal end 14 that mechanically engages the housing 20. In the drawings and in the descriptions that follow, the term "proximal," as is traditional, will refer to the end of the forceps 10 that is closer to the user, while the term "distal" will refer to the end that is farther from the user.

For a more detailed description of the forceps 10 including rotating assembly 80, trigger assembly 70, end effector 100 including jaw members 110 and 120 (and operative components associated therewith), and electrosurgical cable 310 (including line-feed configurations and/or connections), reference is made to commonly owned U.S. Pat. No. 7,150,749 to Dycus et al., filed on Sep. 29, 2009.

Figure 2:
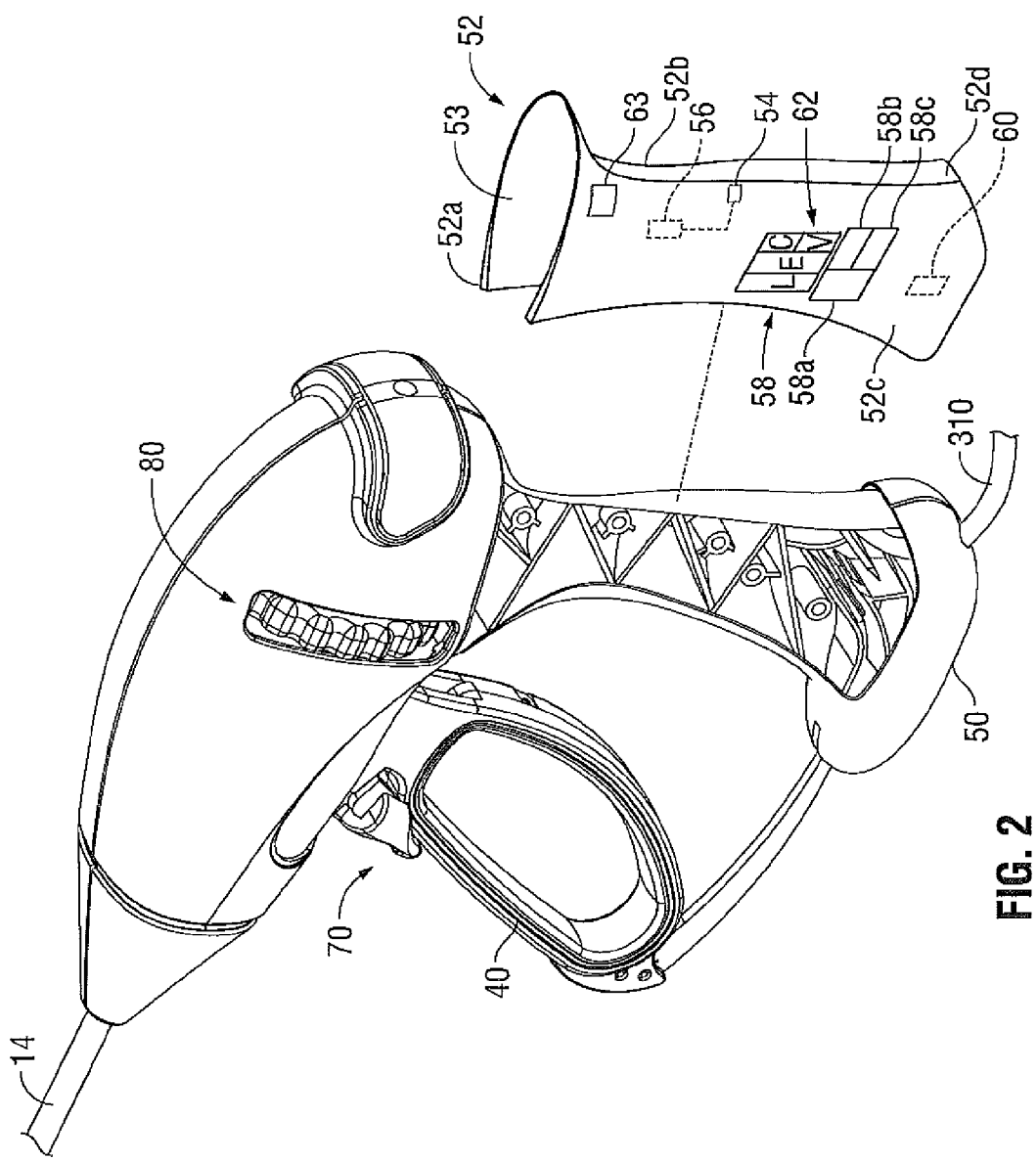
FIG. 2 is an enlarged, rear perspective view of a housing associated with the surgical instrument depicted in FIG. 1.
Figure 3:
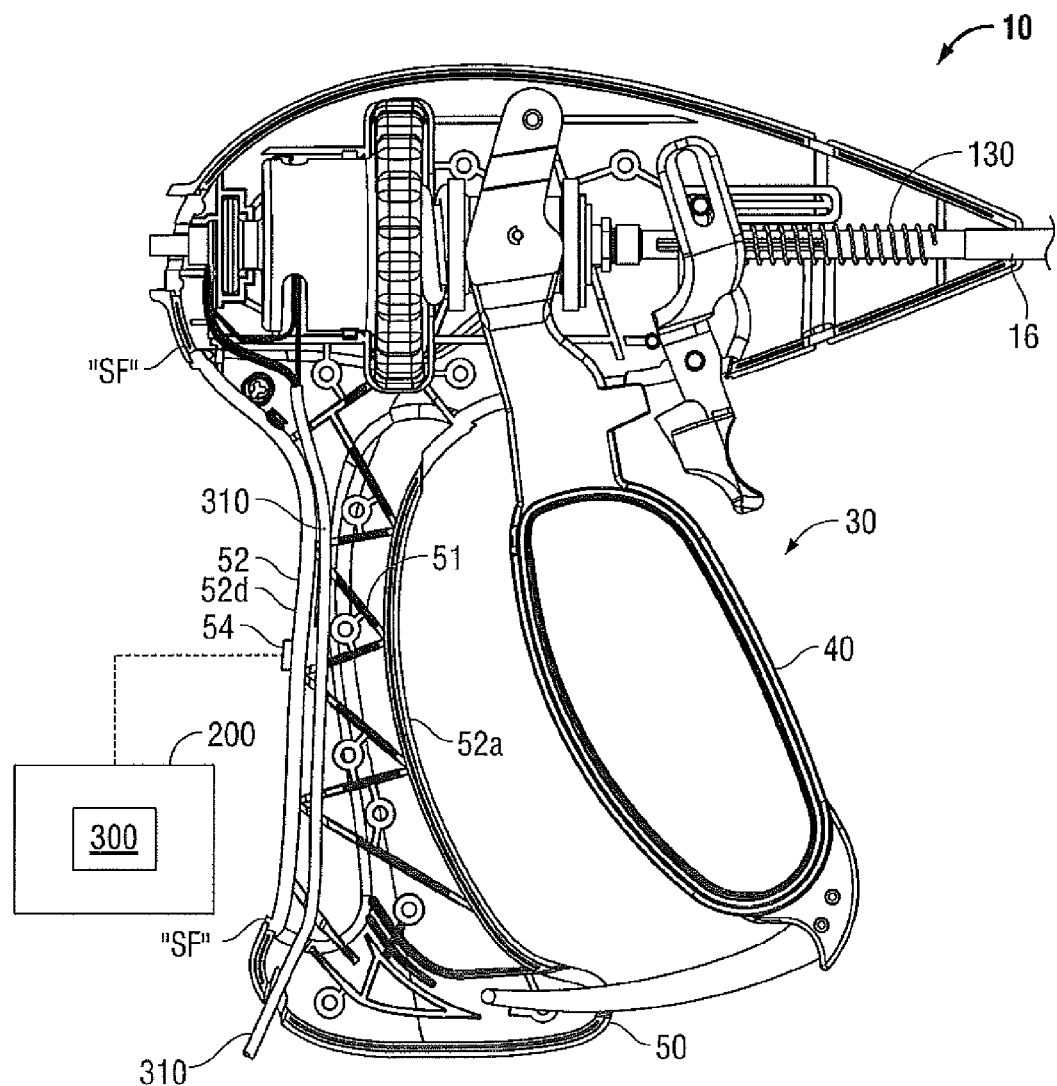
FIG. 3 is an internal, side view of the housing showing the inner-working components associated therewith.

Referring now to FIG. 2, handle assembly 30 includes a fixed handle 50 and a movable handle 40. Movable handle 40 is movable relative to fixed handle 50 and is ultimately connected to the drive assembly 130 (as best seen in FIG. 3), which together mechanically cooperate to impart movement of one or both of the jaw members 110 and 120 to move from an open position, wherein the jaw members 110 and 120 are disposed in spaced relation relative to one another, to a clamping or closed position, wherein the jaw members 110 and 120 cooperate to grasp tissue therebetween. Fixed handle 50 is integrally associated with housing 20. Fixed handle 50 is designed with a common internal frame assembly 51 (FIG. 3) that may include one or more subsystems and/or mechanisms, e.g., gear system, pulley system, linkage system, ratchet mechanism, actuators, relays, solenoids, etc., that are configured to mechanically and/or electrically communicate with one or more functional features associated with one or more selectively removable operator hand grips 52 (grip 52), described in greater detail below. Frame 51 is configured to accommodate variously-sized, shaped configurations of grip 52, i.e., multi-grip components. In the illustrated embodiment, the frame 51 of the fixed handle 50 is configured smaller than an intended size of grip 52.

Grip 52 may be made (or overmolded) from any suitable material including but not limited to plastic, metal, metal alloy, rubber, polymer, etc. In the illustrated embodiment, grip 52 is made from a substantially rigid plastic. Grip 52 includes a grip housing 53 having one or more grip sidewalls or faces, e.g., a finger face 52a, as best seen in FIG. 1; palm face 52b (FIGS. 1 and 2); thumb face 52c (FIG. 2); and a backstrap 52d (FIG. 2). For illustrative purposes, grip 52 is shown including a grip housing having finger face 52a, palm face 52b, thumb face 52c and backstrap 52d. Grip 52 and/or grip housing 53 may include one or more bores or cavities 60 that are configured to accommodate and/or support one or more functional and/or ergonomic features, e.g., actuators, computer readable medium, weighted loads etc., associated therewith. For purposes herein, and unless otherwise specified, operative components associated with the grip 52 are assumed to be disposed in or secured to the one or more cavities 60. Grip 52 may include one or more ergonomically user-friendly features. For example, in certain instances, it may prove useful for one or more of the grip faces, e.g., palm face 52b, of the grip 52 to include a textured or ribbed surface to facilitate gripping thereof.

With continued reference to FIG. 2, grip 52 operably couples to fixed handle 50 and/or the internal frame 51 via one or more suitable coupling methods, e.g., press fit, friction fit, snap-fit, an intent-detent configuration, light-weight or low tack adhesive, etc. In the illustrated embodiment, grip housing 53 including grip faces 52a-52d operably couples to the fixed handle 50 via a snap-fit configuration (illustrated as "SF"). The snap-fit configuration facilitates changing the grip 52, as needed by an end operator of the forceps 10, with little or no effort. Grip 52 may include any suitable shape, size, profile, material, or other physical property so as to create an extension of the frame 51 of the fixed handle 50. Grip 52 may be configured for dedicated right hand, dedicated left hand, or universal (i.e., both right and left hand) use for ergonomic comfort.

Referring to FIG. 3, grip 52 is configured to communicate with generator 200 and/or system 300 via one or more suitable data transfer interfaces, e.g., via a USB connection, for data logging or downloading. In this instance, for example, a USB port 54 may be operably disposed on the grip housing 53 for coupling to a corresponding USB port (not shown) operably disposed on the generator 200 (FIGS. 1 and 3). One or more suitable USB cables may be utilized to couple the USB port 54 to the USB port on the generator 200.

The USB port 54 communicates with one or more modules 56, e.g., a data chip 56 (or other suitable computer readable or storable medium) operably disposed on or associated with the grip 52 (FIG. 1). For illustrative purposes, the grip 52 is shown with one data chip 56 disposed thereon. Information stored on the data chip 56 may include, but is not limited to, specific user settings, data logging of attached surgical instruments, security codes that allow only certain functions or surgical procedures to be performed using a specific grip 52 or limiting usage of a certain grip 52 by count, etc.

Referring back to FIG. 2, grip 52 may include one or more electrical and/or mechanical interfaces that are configured to interact with one or more corresponding electrical and/or mechanical interfaces associated with the forceps 10. For example, in the illustrated embodiment, an actuator 58 includes a plurality of actuators 58a-58c that is in electromechanical communication with one or more functional components of the forceps 10. More particularly, actuator 58a may be in operative communication with the end effector 100 for locking one or both of the jaw members 110 and 120 in one of the open and closed positions. Actuator 58b may be in operative communication with the rotating assembly 80 for imparting (or in some instances preventing) rotational movement thereof. Actuator 58c may be in operative communication with the trigger assembly 70 and may function as a "lock-out" feature, e.g., as a safety switch, that prevents inadvertent actuation thereof.

In the illustrated embodiment, grip 52 includes a plurality of dedicated functionality actuators 62 that are configured to control operation of one or more functional components that may be associated with the forceps 10. For example, in the instance where the forceps 10 includes a lighting feature, the grip 52 includes a corresponding actuator "L." In the instance where the forceps includes an evacuation and/or suction feature, the grip includes a corresponding actuator "E." In the instance where the forceps includes a vision and/or camera feature, the grip includes a corresponding actuator "C/V." As can be appreciated, the foregoing functional features are for illustrative purposes only and are not intended to be limiting.

Grip housing 53 is configured to receive and or support one or more weighted components or loads. More particularly, one or more of the cavities 60 are operably disposed on the grip housing 53 and are configured to receive and support one or more selectively removable weighted components (not explicitly shown). The weighted components may be secured to the cavity 60 as needed to improve operator comfort.

In use, the frame 51 of the fixed handle 50 is, initially, without the grip 52 (FIG. 2). Based on an operator's preference, e.g., right or left handed use, an operator attaches the appropriate grip 52 to the frame 51 (FIGS. 1 and 3). In certain instances, the operator may secure one or more weighted components to the cavity 60 to balance the forceps 10; this is intended to provide additional comfort for the operator. Prior to the surgical procedure, the operator connects the grip 52, via the USB cable, to the generator 200 to communicate therewith for downloading and/or data logging of the specific information contained on the data chip 56 of the grip 52, e.g., surgical procedure to be performed. System 300 of the generator 200 reads relevant information from the data chip 54 and subsequently programs the generator 200 as required. In certain instances, prior to carrying out the surgical procedure, the operator may disconnect the USB cable from the port 54. Thereafter, the operator utilizes the forceps 10 for the specific surgical procedure. Subsequently, the operator may reestablish communication between the grips 52 and generator 200 for downloading and/or data logging of the specific information contained on the data chip 56 of the grip 52, e.g., usage count of the grips 52 and/or forceps 10, time of use of the forceps 10, etc.

From the foregoing and with reference to the various figure drawings, those skilled in the art will appreciate that certain modifications can also be made to the present disclosure without departing from the scope of the same. For example, in embodiments, grip 52 may include robotic or automation attachment features for non-human operation of the forceps 10.

In some embodiments, grip 52 may be configured for custom fits for particular surgeons based on molds, hand sizing, etc. Grip 52 may be custom fit to include specific locations of actuators or actuation elements, e.g., triggers, intensity dials, toggles, etc.

In some embodiments, grip 52 (or operative component(s) associated therewith, e.g., data chip 56) may be configured to store information relevant to a particular surgeon. In this instance, the generator 200 may be configured read the data from the grip 52, i.e., recognize surgeon, and set preferred or particular settings for that surgeon. In certain instances, the generator 200 may recommend specific settings based on a particular surgeon. The generator 200 may be configured to actively acknowledge surgeon. In this instance, the generator 200 may prompt a surgeon to enter a password. Generator 200 and/or grip 52 may be configured to store surgeon information for manufacturer, e.g., usages, preferred settings, surgical techniques, e.g., activation, rotation, gripping techniques, and sequencing.

In some embodiments, grip 52 may be configured to automatically deactivate activation switches, which may be operably associated with the forceps 10, after an initial use thereof.

In some embodiments, grip 52 may include pressure sensors 63 that relay usage information back to generator 200 for future manufacture use and research and development.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
a housing having a shaft that extends therefrom that defines a longitudinal axis therethrough, and supports an end effector having opposing jaw members at a distal end thereof;
a handle assembly including a movable handle configured to impart movement of at least one of the jaw members operably associated with the end effector and a fixed handle including an internal frame assembly adapted to couple to at least one selectively removable hand grip,
wherein the at least one selectively removable hand grip includes at least one data chip in communication with a USB port disposed on the hand grip,
wherein the at least one selectively removable hand grip further includes at least one cavity defined therein configured to removably receive a load that is weighted to balance one of the at least one selectively removable hand grip and surgical instrument.

2. The surgical instrument according to claim 1, wherein the at least one selectively removable hand grip is configured to operably couple to a source of electrosurgical energy that supplies electrosurgical energy to the electrosurgical instrument.

3. The surgical instrument according to claim 1, wherein the at least one data chip includes information pertaining to at least one of a specific user's settings; data logging of one of the at least one selectively removable hand grip and electrosurgical instrument; security codes allowing one of certain functions and surgical procedures to be performed when the at least one selectively removable hand grip is coupled to the electrosurgical instrument; and a usage limiter count.

4. An electrosurgical system for performing an electrosurgical procedure, comprising:
an electrosurgical generator including a control system;
an electrosurgical instrument adapted to couple to the electrosurgical generator, the electrosurgical instrument including:
a housing having a shaft that extends therefrom that defines a longitudinal axis therethrough, and supports an end effector having opposing jaw members at a distal end thereof;
a handle assembly including a movable handle configured to impart movement of at least one of the jaw members operably associated with the end effector and a fixed handle including an internal frame assembly adapted to couple to at least one selectively removable hand grip,
wherein the at least one selectively removable hand grip includes at least one data chip in communication with a USB port disposed on the hand grip,
wherein the at least one selectively removable hand grip further includes at least one cavity defined therein configured to removably receive a load that is weighted to balance one of the at least one selectively removable hand grip and surgical instrument.

5. The electrosurgical system according to claim 4, wherein the at least one data chip includes information pertaining to at least one of: a specific user's settings; data logging of one of the at least one selectively removable hand grip and electrosurgical instrument; security codes allowing one of certain functions and surgical procedures to be performed when the at least one selectively removable hand grip is coupled to the electrosurgical instrument; and a usage limiter count.

6. The method of performing a surgical procedure, the method comprising:
providing a surgical instrument including:
a housing having a shaft that extends therefrom that defines a longitudinal axis therethrough, and supports an end effector having opposing jaw members at a distal end thereof;
a handle assembly including a movable handle configured to impart movement of at least one of the jaw members operably associated with the end effector and a fixed handle including an internal frame assembly adapted to couple to at least one selectively removable hand grip, wherein the at least one selectively removable hand grip includes at least one data chip operatively associated therewith;

selecting an appropriate grip for attaching to the handle assembly based on the operator's preference;

securing one or more weighted components to the cavity to balance the selected hand grip;

connecting the selected grip to a generator to communicate therewith;

downloading specific information contained on the data chip of the grip to the generator thereby programming the generator; and utilizing the surgical instrument for the specific surgical procedure.

7. The method according to claim 6, wherein the at least one selectively removable hand grip further includes at least one cavity defined therein.

* * * * *